United States Patent
Wang et al.

(10) Patent No.: US 6,900,352 B1
(45) Date of Patent: May 31, 2005

(54) SIX-MEMBERED CHIRAL PHOSPHINE LIGANDS

(75) Inventors: Zeng Fu Wang, Louisville, KY (US); Kexin Yang, Louisville, KY (US); Boliang Lou, Louisville, KY (US)

(73) Assignee: Advanced SynTech, LLC, Louisville, KY (US)

( * ) Notice: Subject to any disclaimer, the term of this patent is extended or adjusted under 35 U.S.C. 154(b) by 71 days.

(21) Appl. No.: 10/374,659

(22) Filed: Feb. 25, 2003

Related U.S. Application Data

(60) Provisional application No. 60/359,285, filed on Feb. 25, 2002.

(51) Int. Cl.$^7$ ................................................ C07F 9/547
(52) U.S. Cl. ............................ 564/13; 564/12; 564/16; 568/12
(58) Field of Search ............................ 564/12, 13, 16; 568/12

(56) References Cited

U.S. PATENT DOCUMENTS

| | | |
|---|---|---|
| 5,202,493 A | 4/1993 | Burk |
| 5,521,281 A | 5/1996 | Sen et al. |
| 5,532,395 A | 7/1996 | Burk |
| 5,807,872 A | 9/1998 | Shih et al. |
| 5,936,109 A | 8/1999 | Berens |
| 6,172,249 B1 | 1/2001 | Berens et al. |
| 6,337,406 B1 | 1/2002 | Zhang |

OTHER PUBLICATIONS

BRN 3877114 abs of J. Chem Soc by Mann et al pp 3039–42 1952.*
CA:110:83109 abs of Izvestiya Akademii Nauk SSSR Seriya Khimicheskaya by Prokof ev et al (9) pp 2074–80 1988.*
CA:82:98077 abs of Tetrahedron Letters by S. Samaan (45) pp 3927–30 1974.*
CA:91:175450 abs of Phosphorus and Sulfur and the related elements by S. Samaan 7(1) pp 89–94 1979.*

* cited by examiner

Primary Examiner—Porfirio Nazario-Gonzalez
(74) Attorney, Agent, or Firm—Stites & Harbison PLLC; John E. Vanderburgh

(57) ABSTRACT

A novel class of chiral phosphine ligands useful for producing catalyst for asymmetric reactions with general structure of Formula 1:

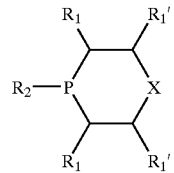

Formula 1

9 Claims, No Drawings

SIX-MEMBERED CHIRAL PHOSPHINE LIGANDS

REFERENCE TO RELATED APPLICATIONS

This application claims priority under provisional application 60/359,285, filed Feb. 25, 2002, entitled SIX MEMBERED CHIRAL PHOSPHINE LIGANDS which is incorporated by reference herein.

FIELD OF INVENTION

The present invention relates to a novel class of six membered heterocycle chiral phosphine ligands, methods that can be used to prepare these ligands, and their potential applications for use with transition metal compounds as catalysts in asymmetric reactions.

BACKGROUND OF INVENTION

Advances of pharmaceutical science revealed that biological system has the ability of distinguishing individual members of a pair of enantiomeric compounds, and thus giving different responses. In other words, the receptor sites in biological systems have three-dimensional surface structure that consists of distinct grooves and cavities. These receptors interact only with three-dimensional molecules with complementary structures. Therefore, depending on the steric conformation of the molecule that links to the receptor, the biological results may vary significantly. One enantiomer may demonstrate highly potent therapeutic power towards certain disease while the other enantiomer is either inactive or highly toxic. For example, Thalidomide, a widely used sedative by many pregnant women in the 1960s, was identified as teratogenic. It was found that the feto-toxic activity was only associated with one of the enantiomers, the S-form. The other enantiomer, the R-Thalidomide, could be a safe drug theoretically. On the other hand, processes that produce only the desired enantiomers are more cost effective than those that produce racemic mixtures since the costs related to separation of the two enantiomers from the racemic mixture are avoided. To prevent a repetition of tragedy like Thalidomide, reduce production cost, and meet increasingly restrict FDA guidlines, tremendous effort has been directed towards developing highly efficient and reliable process for production of desired molecule in enantiomerically pure state. It has been estimated that more than 50% of the top-selling drugs are enantiomerically pure, and up to 80% of drugs currently under development are chiral. Of all available methods, chiral catalyst mediated asymmetric synthesis is one of the most efficient, versatile, cost effective, and environment friendly processes to obtain enantiomerically pure compounds, which has been evidenced by the explosive growth of research reports in this area and recent awarding of 2001 Nobel prize in chemistry to William S. Knowles, Ryoji Noyori and K. Barry Sharpless for their pioneering research work in asymmetric synthesis using chiral catalyst. In addition to its widespread applications in basic research and pharmaceutical industry, asymmetric catalysis is also used extensively in other industries such as agrochemical, animal health, flavor and fragrance, liquid crystal material, and polymer, etc.

Generally, the chiral catalysts used in many asymmetric reactions consist of transition metals and chiral ligands. In most cases, the asymmetric transformations were accomplished via a preferred asymmetric transition state derived mainly under the influence of the chiral ligand. The unique chiral structure of ligand was essential for the activity, enantioselectivity, and lifetime of a given catalyst. Chiral phosphine ligands have been an integral part of many successful chiral catalysts used in asymmetrical catalysis. However, factors vital to catalyst activity, stereoselectivity, and lifetime are often reaction specific and not well understood. Tremendous effort has been directed towards is design and synthesis of chiral phosphine ligands to maximize activity, stereoselectivity, and lifetime of chiral catalysts. A comprehensive review article on phosphine ligand was recently published (Laurenti, D. and Santelli, M. *Org. Prep. Proc.* 1999, 31(3), 245–294.).

SUMMARY OF INVENTION

The present invention describes a novel class of chiral phosphine

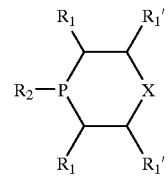

ligands with general structure of Formula 1, wherein

X is selected from a group consisting of oxygen, sulfur, methylene (—$CH_2$—), —$NR_3$, $PR_3$, $AsR_3$ and $SbR_3$;

$R_1$ is selected from a group consisting of substituted alky, substituted cycloalkyl, substituted heterocyclyl, substituted alkenyl, substituted alkynyl, substituted aryl and substituted alkylaryl;

$R_1'$ is selected from a group consisting of hydrogen, substituted alkyl, substituted cycloalkyl, substituted cycloheteroalkyl, substituted alkenyl, substituted alkynyl, substituted aryl and substituted alkylaryl;

$R_2$ is selected from a group consisting of substituted alkyl, substituted cycloalkyl, substituted heterocyclyl; substituted cycloheteroalkyl, substituted alkenyl, substituted aryl, substituted heteroaryl, substituted alkylaryl and substituted alkylheteroaryl;

$R_3$ is selected from a group consisting of hydrogen, substituted alkyl, substituted cycloalkyl, substituted cycloheteroalkyl, substituted alkenyl, substituted alkynyl, substituted aryl, substituted alkylaryl, substituted heteroaryl and substituted alkylheteroaryl; or $R_3$ is selected from a group consisting of substituted alkyl sulfonyl, substituted aryl sulfonyl, substituted alkyl carboxyl, substituted aryl carboxyl, substituted alkoxyl carboxyl, substituted aroxyl carboxyl substituted alkyl carboxamido, substituted aryl carboxamido, substituted alkylthio carboxamido and substituted arylthio carboxamido;

When $R_2$ is a spacer, defined herein as molecules that have two appropriate functional groups capable of attaching with phosphorus atoms on two of the six-membered rings, an important class of bidentate ligands with structure of Formula 2 are produced:

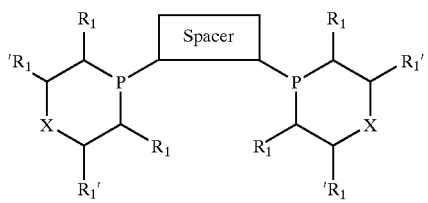

Formula 2 where:
X is selected from a group consisting of oxygen, sulfur, methylene (—CH$_2$—), —NR$_3$, PR$_3$, AsR$_3$ and SbR$_3$;
R$_1$ is selected from a group consisting of substituted alkyl, substituted alkenyl, substituted alkynyl, substituted aryl and substituted alkylaryl;
R$_1$' is selected from a group consisting of hydrogen, substituted alkyl, substituted alkenyl, substituted alkynyl, substituted aryl and substituted alkylaryl;
R$_3$ is selected from a group consisting of hydrogen, substituted alkyl, substituted alkenyl, substituted alkynyl, substituted aryl, substituted alkylaryl, substituted heteroaryl and substituted alkylheteroaryl; or
R$_3$ is selected from a group consisting of substituted alkyl sulfonyl, substituted aryl sulfonyl, substituted alkyl carboxyl, substituted aryl carboxyl, substituted alkoxyl carboxyl, substituted aroxyl carboxyl substituted alkyl carboxamido, substituted aryl carboxamido, substituted alkylthio carboxamido and substituted arylthio carboxamido;
Spacer may be the following:
—(CH$_2$)$_n$—, where n is an integer ranging from 2 to 6; or
—(CH$_2$)$_m$X(CH$_2$)$_n$—, where m and n are integers ranging from 1 to 6;
X is selected from a group consisting of oxygen, sulfur, methylene (—CH$_2$—), —NR$_3$, PR$_3$, AsR$_3$, SbR$_3$; or
1,2-divalent phenyl; 1,2-divalent phenyl substituted with alkyl (with 1 to 8 carbon atoms), aryl, alkyl aryl, heteroaryl, alkyl heteroaryl; or
1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl and substituted alkylheteroaryl; or
1,2-divalent napthyl; 1,2-divalent napthyl substituted with alkyl (with 1 to 8 carbon atoms), aryl, alkyl aryl, heteroaryl, alkyl heteroaryl; or
1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl, substituted alkylheteroaryl; or
2,3-divalent napthyl; 2,3-divalent napthyl substituted with alkyl (with 1 to 8 carbon atoms), aryl, alkyl aryl, heteroaryl, alkyl heteroaryl; or
1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl, substituted alkylheteroaryl; or
1,8-divalent napthyl; 1,8-divalent napthyl substituted with alkyl (with 1 to 8 carbon atoms), aryl, alkyl aryl, heteroaryl, alkyl heteroaryl; or
1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl, substituted alkylheteroaryl;
2,2'-divalent 1,1'-biphenyl; 2,2'-divalent 1,1'-biphenyl substituted with alkyl (with 1 to 8 carbon atoms), aryl, alkyl aryl, heteroaryl, alkyl heteroaryl; or 1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl, or substituted alkylheteroaryl;
2,2'-divalent 1,1'-binapthyl; 2,2'-divalent 1,1'-binapthyl substituted with alkyl (with 1 to 8 carbon atoms), aryl, alkyl aryl, heteroaryl, alkyl heteroaryl; or 1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl and substituted alkylheteroaryl;
1,1'-divalent ferrocene; 1,1'-divalent ferrocene substituted with alkyl (with 1 to 8 carbon atoms), aryl, alkyl aryl, heteroaryl, alkyl heteroaryl; or 1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl and substituted alkylheteroaryl;
1,2-divalent heteroaryl; 1,2-divalent heteroaryl substituted with alkyl (with 1 to 8 carbon atoms), aryl, alkyl aryl, heteroaryl, alkyl heteroaryl; or 1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl and substituted alkylheteroaryl;
1,2-divalent fused heteroaryl; 1,2-divalent fused heteroaryl substituted with alkyl (with 1 to 8 carbon atoms), alkyl, alkyl aryl, heteroaryl, alkyl heteroaryl; or 1,2-divalent phenyl substituted with heteroatom groups such as F, Cl, Br, I, OR, CN, NO$_2$, NR$_2$, SR, AsR$_2$, SbR$_2$, CO$_2$R, SO$_2$R, PO$_3$R, where R is selected from a group consisting of hydrogen, substituted alkyl, substituted aryl substituted alkylaryl, substituted heteroaryl and substituted alkylheteroaryl.

The chiral phosphine ligands of the present invention may be complexed with a transition metal to provide a catalyst for asymmetric synthesis, such as asymmetric hydrogenation. The chiral ligand catalyst complexes can be used in the asymmetrical synthesis of pharmaceutical compounds as well as synthesis of compounds for industrial applications where steriochemical control is of utmost importance.

DETAILED DESCRIPTION OF THE INVENTION

As used above, and through the description of the invention, the following terms, unless otherwise indicated, shall be understood to have the following meanings:

"Alkyl" means a saturated aliphatic hydrocarbon group which may be straight or branched and having about 1 to about 20 carbons in the chain. Branched means that a lower alkyl group such as methyl, ethyl, or propyl is attached to a linear alkyl chain. Preferred straight or branched alkyl groups are the "lower alkyl" groups which are those alkyl groups having from 1 to about 6 carbon atoms.

"Alkenyl" means an aliphatic hydrocarbon group defined the same as for "alkyl" plus at least one double bond between two carbon atoms anywhere in the hydrocarbon.

"Alkynyl" means an aliphatic hydrocarbon group defined the same as for "alkyl" plus at least one triple bond between two carbon atoms anywhere in the hydrocarbon.

"Aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art. Aryl thus contains at least one ring having at least 5 atoms, with up to two such rings being present, containing up to 10 atoms therein, with alternating (resonating) double bonds between adjacent carbon atoms. Aryl groups may likewise be substituted with 0–3 groups selected from $R_1$, $R_2$ or $R_3$ The definition of aryl includes but is not limited to phenyl, biphenyl, indenyl, fluorenyl, naphthyl (1-naphtyl, 2-naphthyl).

Heteroaryl is a group containing from 5 to 10 atoms, 1–4 of which are heteroatoms, 0–4 of which heteroatoms are nitrogen, and 0–1 of which are oxygen or sulfur, said heteroaryl groups being substituted with 0–3 groups selected from $R_s$.

The definition of heteroaryl includes but is not limited to pyridyl, furyl, thiophenyl, indolyl, thiazolyl, imidazolyl, benzimidazolyl, tetrazolyl, pyrazinyl, pyrimidyl, quinolyl, isoquinolyl, benzofuryl, isothiazolyl, benzothienyl, pyrazolyl, isoindolyl, isoindolyl, purinyl, carbazolyl, oxazolyl, benzthiazolyl, benzoxazolyl, quinoxalinyl, quinazolinyl, and indazolyl.

"Cycloalkyl" means a saturated carbocyclic group having one or more rings and having 3 to about 10 carbon atoms. Preferrd cycloalkyl groups include cyclopropyl, cyclobutyl, cyclopentyl, cyclohexyl, cycloheptyl, and decahydronaphthyl.

"heterocyclyl" means an about 4 to about 10 member monocyclic or multicyclic ring system wherein one or more of the atoms in the ring system is an element other than carbon chosen amongst nitrogen, oxygen or sulfur. The heterocyclyl may be optionally substituted by one or more alkyl group substituents. Examplary heterocyclyl moieties include quinuclidine, pentamethylenesulfide, tetrahedropyranyl, tetrahydrothiophenyl, pyrrolidinyl or tetrahydrofuranyl.

"Saturated" means that the atom possesses the maximum number of single bonds either to hydrogen or to other atoms, eg. a carbon atom is $sp^3$ hybridized.

"Unsaturated" means that the atom possesses less than the maximum number of single bonds either to hydrogen or to other atoms, eg. a carbon atom is $sp^2$ or $Sp^3$ hybridized.

"Substituted" means the attachment of any of the following groups, including:
(i) H
(ii) alkyl
(iii) aryl
(iv) amino, amidino, bromo, chloro, carboxy, carboxamido, thiocarboxy, cyano, fluoro, guanidino, hydroxy, iodo, nitro, oxo, thiol, trihalomethyl, trihalomethoxy
(v) N—($C_1$–$C_6$alkyl)amidino and N-aryl amidino
(vi) N—($C_1$–$C_6$alkyl)guanidino and N-aryl guanidino
(vii) $C_1$–$C_6$alkylamino and arylamino
(viii) N,N'-($C_1$–$C_6$dialkyl)amino, N,N'-diarylamino and N—($C_1$–$C_6$alkyl)-N'-(aryl)-amino
(ix) $C_1$–$C_6$alkylarylamino and aryl$C_1$–$C_6$alkylamino
(x) 4-, 5-, 6-, or 7-membered azacycloalkanes
(xi) $C_1$–$C_6$alkyloxy and aryloxy
(xii) $C_1$–$C_6$alkylaryloxy and aryl$C_1$–$C_6$alkyloxy
(xiii) $C_1$–$C_6$alkylarylthio and aryl$C_1$–$C_6$alkylthio
(xiv) $C_1$–$C_6$alkylcarbonyl and arylcarbonyl
(xv) $C_1$–$C_6$alkylarylcarbonyl and aryl$C_1$–$C_6$alkylcarbonyl
(xvi) $C_1$–$C_6$alkoxycarbonyl and aryloxycarbonyl
(xvii) $C_1$–$C_6$alkylaryloxycarbonyl and aryl$C_1$–$C_6$alkyloxycarbonyl
(xviii) $C_1$–$C_6$alkylarylthiocarbonyl and aryl$C_1$–$C_6$alkylthiocarbonyl
(xix) N-mono-($C_1$–$C_6$alkyl) and N,N'-di-($C_1$–$C_6$alkyl) aminocarbonyl
(xx) N-mono-(aryl) and N,N'-di-(aryl)aminocarbonyl
(xxi) N,N'-($C_1$–$C_6$alkyl)(aryl)aminocarbonyl
(xxii) N-mono-($C_1$–$C_6$alkylaryl) and N,N'-di-(aryl$C_1$–$C_6$alkyl)aminocarbonyl
(xxiii) N,N'-($C_1$–$C_6$alkyl)(aryl$C_1$–$C_6$alkyl)aminocarbonyl
(xxiv) N,N'-(aryl)(aryl$C_1$–$C_6$alkyl)aminocarbonyl
(xxv) $C_1$–$C_6$alkylcarbonylamino and arylcarbonylamino
(xxvi) $C_1$–$C_6$alkylarylcarbonylamino and aryl$C_1$–$C_6$alkylcarbonylamino
(xxvii) $C_1$–$C_6$alkoxycarbonylamino and aryloxycarbonylamino
(xxviii) $C_1$–$C_6$alkyaryloxycarbonylamino and aryl$C_1$–$C_6$alkyloxycarbonylamino
(xxix) $C_1$–$C_6$alkylarylthiocarbonylamino and aryl$C_1$–$C_6$alkylthiocarbonylamino
(xxx) N-mono-($C_1$–$C_6$alkyl) and N,N'-di-($C_1$–$C_6$alkyl) aminocarbonylamino
(xxxi) N-mono-(aryl) and N,N'-di-(aryl) aminocarbonylamino
(xxxii) N,N'-($C_1$–$C_6$alkyl)(aryl)aminocarbonylamino
(xxxiii) N-mono-($C_1$–$C_6$alkylaryl) and N,N'-di-(aryl$C_1$–$C_6$alkyl)aminocarbonylamino
(xxxiv) N,N'—$C_1$–$C_6$alkyl) (aryl$C_1$–$C_6$alkyl) aminocarbonylamino
(xxxv) N,N'-(aryl)(aryl$C_1$–$C_6$alkyl)aminocarbonylamino
(xxxvi) $C_1$–$C_6$alkylcarbonyloxy and arylcarbonyloxy
(xxxvii) $C_1$–$C_6$alkylarylcarbonyloxy and aryl$C_1$–$C_6$alkylcarbonyloxy
(xxxviii) $C_1$–$C_6$alkoxycarbonyloxy and aryloxycarbonyloxy
(xxxix) $C_1$–$C_6$alkylaryloxycarbonyloxy and aryl$C_1$–$C_6$alkyloxy-carbonyloxy
(xl) $C_1$–$C_6$alkylarylthiocarbonyloxy and aryl$C_1$–$C_6$alkylthiocarbonyloxy
(xli) N-mono-($C_1$–$C_6$alkyl) and N,N'-di-($C_1$–$C_6$alkyl) aminocarbonyloxy
(xlii) N-mono-(aryl) and N,N'-di-(aryl)aminocarbonyloxy
(xliii) N,N'-($C_1$–$C_6$alkyl)(aryl)aminocarbonyloxy
(xliv) N-mono-($C_1$–$C_6$alkylaryl) and N,N'-di-(aryl$C_1$–$C_6$alkyl)amino-carbonyloxy
(xlv) N,N'-($C_1$–$C_6$alkyl) (aryl$C_1$–$C_6$alkyl) aminocarbonyloxy and N,N'-(aryl)(aryl$C_1$–$C_6$alkyl) aminocarbonyloxy
(xlvi) $C_1$–$C_6$alkylsulfoxy and arylsulfoxy
(xlvii) $C_1$–$C_6$alkylarylsulfoxy and aryl$C_1$–$C_6$alkylsulfoxy
(xlviii) $C_1$–$C_6$alkylsulfonyl and aryl sulfonyl
(xlix) $C_1$–$C_6$alkylarylsulfonyl and aryl$C_1$–$C_6$alkylsulfonyl
(l) $C_1$–$C_6$alkylsulfonamido and arylsulfonamido
(li) $C_1$–$C_6$alkylarylsulfonamido and aryl$C_1$–$C_6$alkylsulfonamido (lii) $C_1-C_6$alkylaminosulfonyl and arylaminosulfonyl
(liii) $C_1-C_6$alkylaminosulfonyl and aryl$C_1-C_6$alkylaminosulfonyl
(liv) $C_1-C_6$alkylaminosulfonamido and arylaminosulfonamido
(lv) $C_1-C_6$alkylarylsulfonamido and aryl$C_1-C_6$alkylsulfonamido "Alkyl" and "aryl" used for any of the groups in the above list also means substituted alkyl or substituted aryl, where substituted means groups selected from the same list.

Preparation of Ligands

The present invention also describes approaches towards the synthesis of these ligands. There are some important features demonstrated in our synthetic strategies. First of all, the synthetic strategy was designed to position the chiral centers next to the phosphrous atom, which will creates the required chiral environment in the immediate vicinity of the metal coordnation sphere. Secondly, the proposed synthetic strategies allow a variety of substituents, $R_1$ and $R_2$, be introduced into the chiral centers and the phosphrous atom of the ligand molecule, thus, steric, electronic and physical properties of the ligand could be adjusted in a systematic fashion to maximize the activity, stereoselectivity, and life-time of the catalyst formed with transition metals. Thirdly, we incorporated a third diversity point, X, at a position relatively far away from the metal coordnation site. This diversity point X will not only allow for synthesis of diverse sets of catalysts, but also can be used to modify physical properties of a given catalyst, for example, attaching appropriate side chains to improve soluability, or attaching catalyst to polymer support, etc. The ligands are intended to form catalysts for uses in asymmetric reactions, including but not limited to reactions such as, for example, hydrogenation, hydroboration and Diels-Alder.

The synthesis of ligand Formula 1 is outlined in Schemes 1–11.

Scheme 1

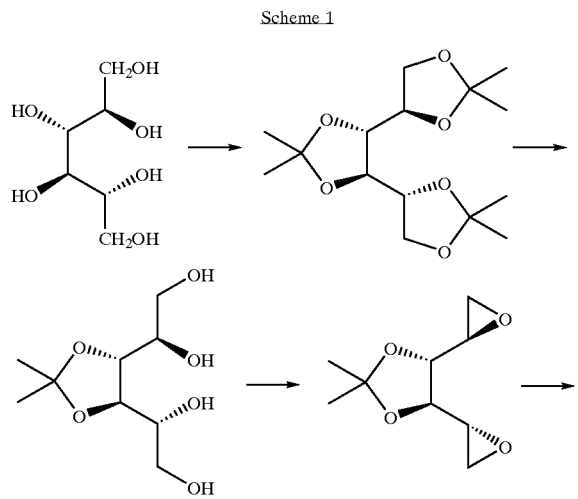

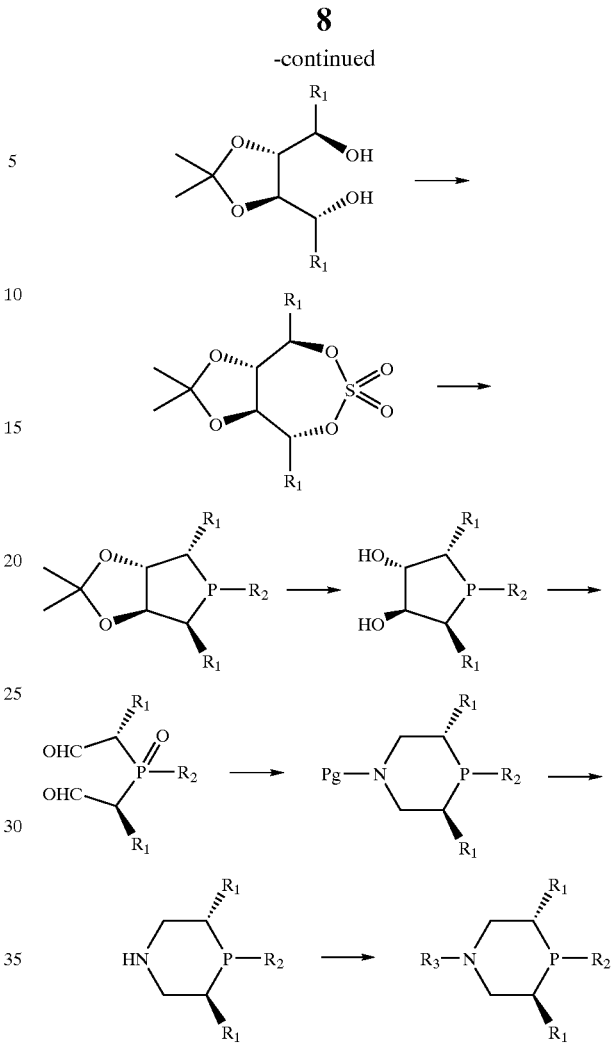

Scheme 2

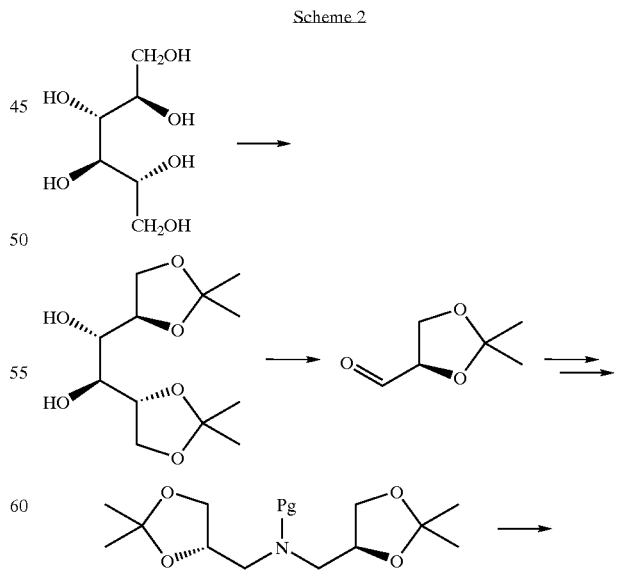

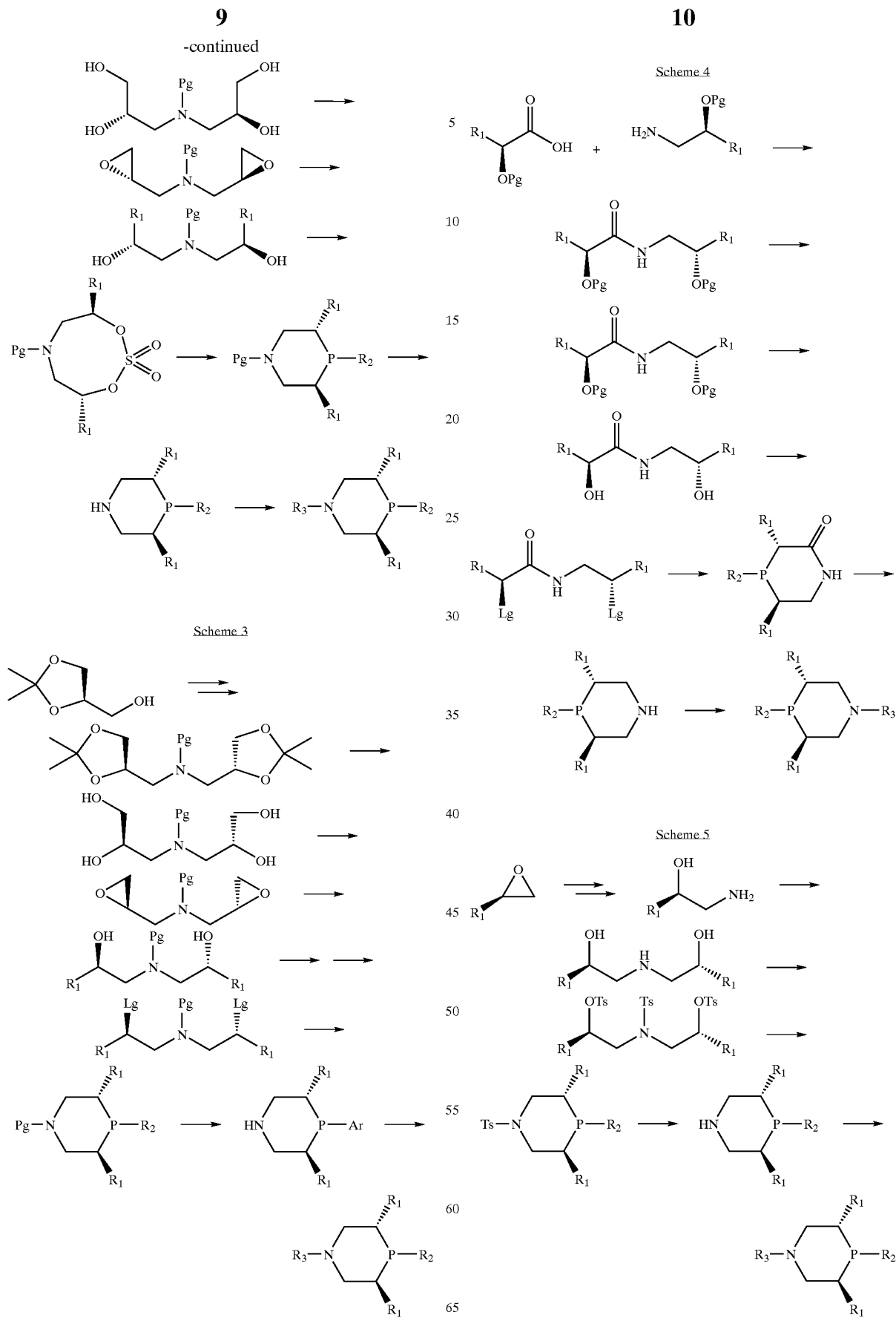

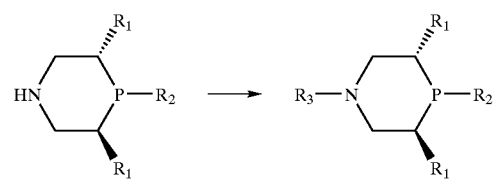
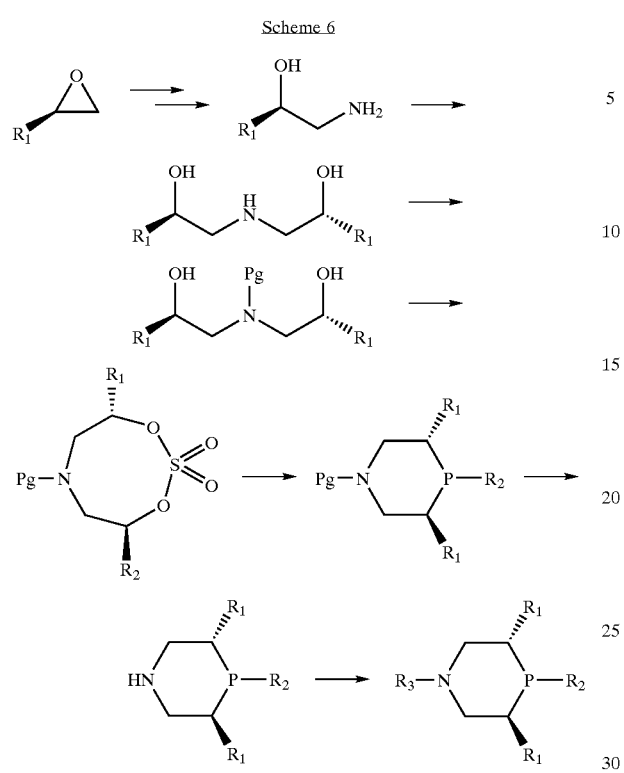

-continued

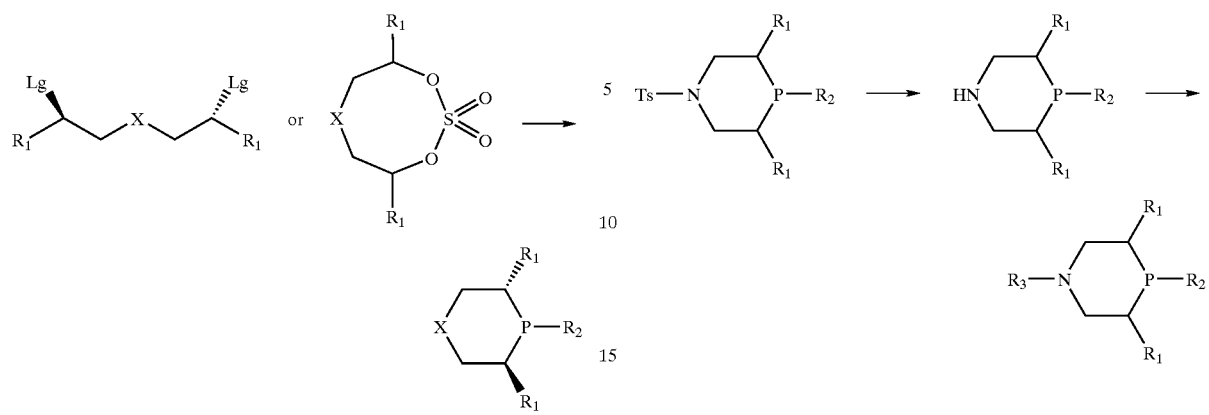

Scheme 10

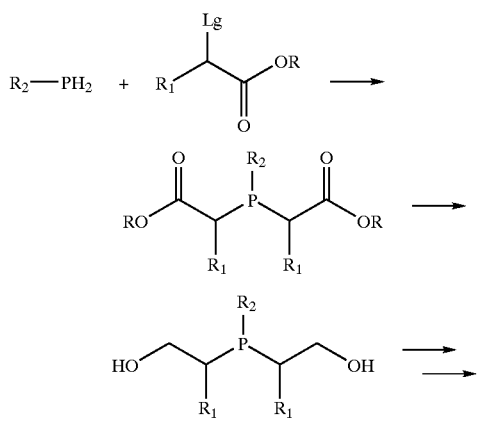

Scheme 11

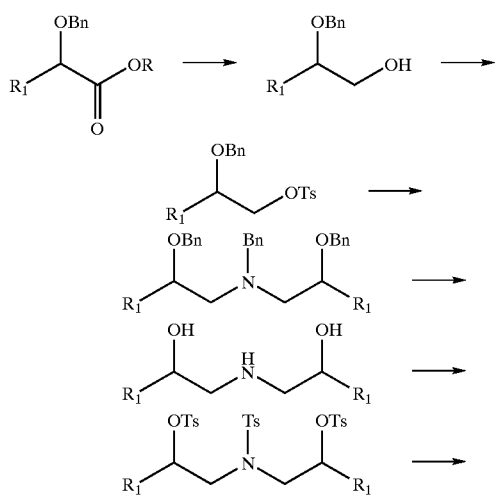

-continued

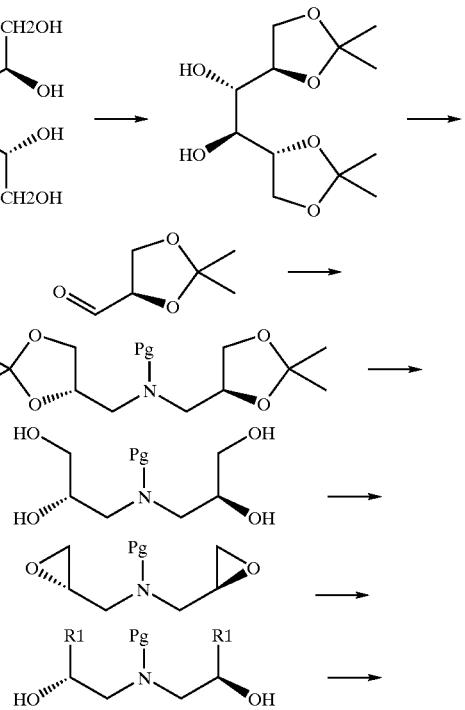

When the monophosphine, $R_2PH_2$, is replaced with bisphosphine, for example, 1,2-phenylbisphosphine, an important class of bidentate ligands with structure of Formula 2 can be prepared using strategies, including but not limited to those showed in schemes 1–11.

In preparing the phosphine ligands of the invention an intermediate is prepared from a chiral building block selected from the group consisting of α-amino derivatives, α-hydroxyl acid derivatives and carbohydrate derivatives. The intermediate includes at least two leaving groups selected from the group consisting of tosylate, mesolate, halide and sulfate.

Representative approaches for synthesis of bidentate ligands Formula 2 are shown in Scheme 12 and Scheme 13.

Scheme 12

15
-continued
16
-continued
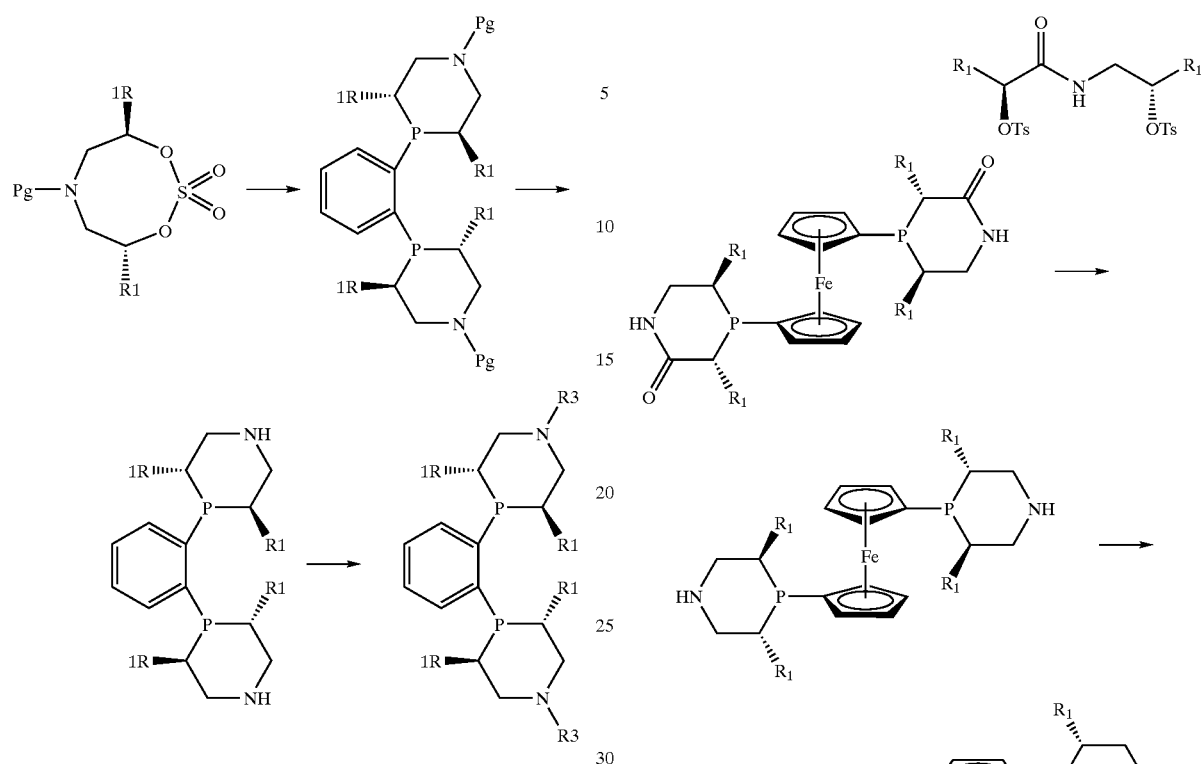
Scheme 13
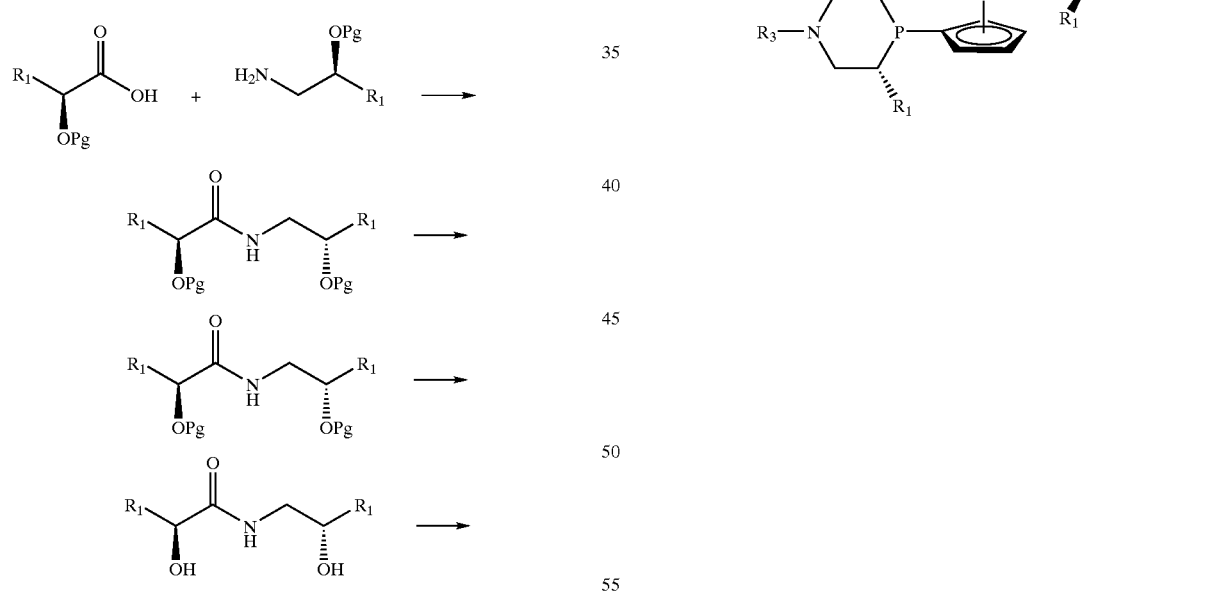
Scheme 14
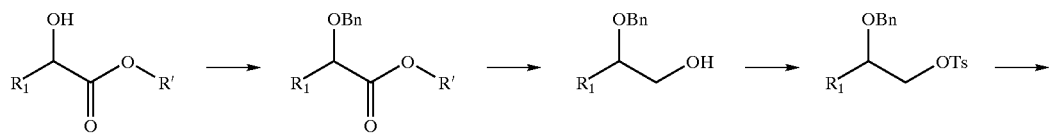

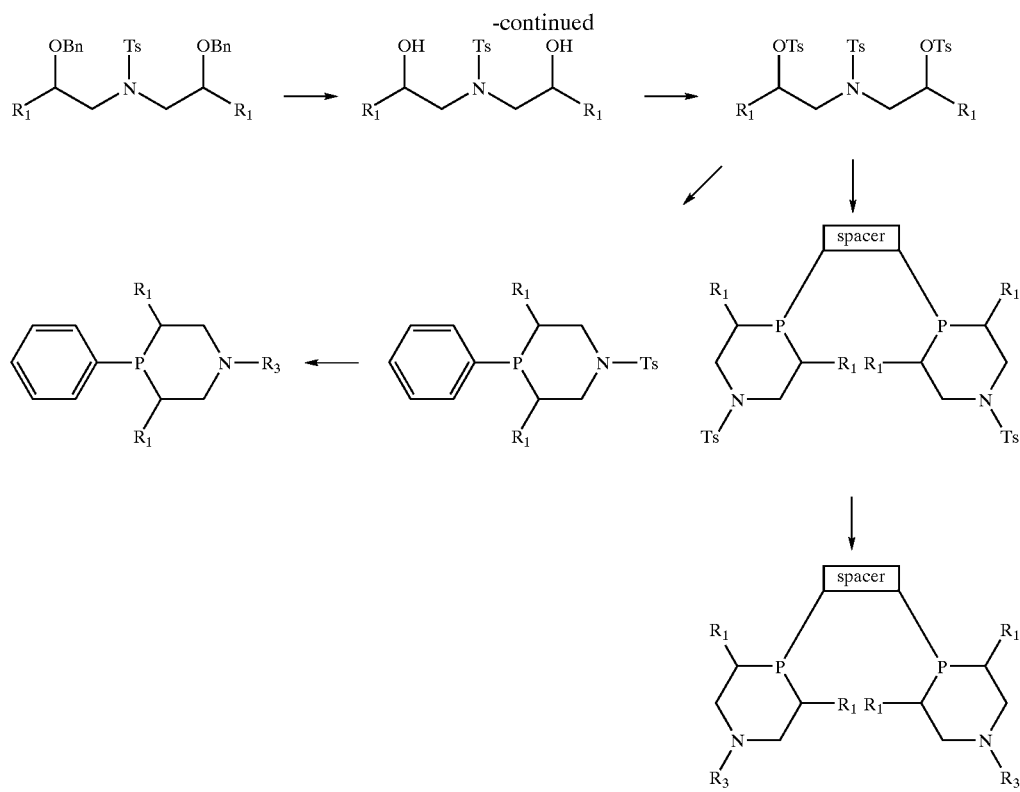
where Bn is benzene and Ts is tosylate.
EXAMPLES
Some representative chiral ligands that can be prepared according to approaches illustrated in Scheme 1–13 are shown below.
The following examples were prepared based on the procedures described in Scheme 14:
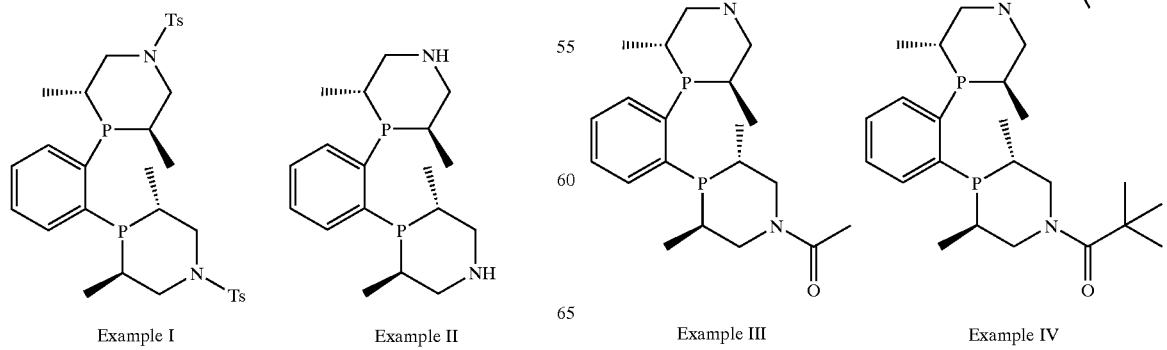
Example I  Example II  Example III  Example IV

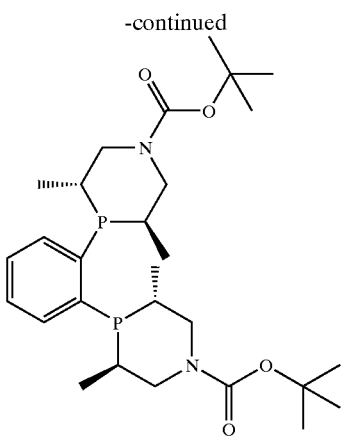

Example V

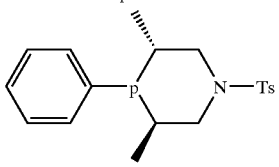

Example VI

Example I

The intermediate of this example was prepared in accordance with the following scheme:

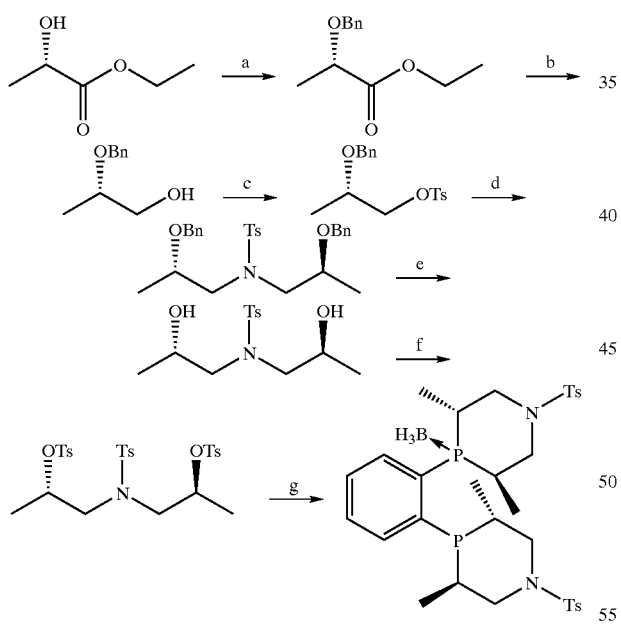

a) Protecting of the Secondary Hydroxyl Group: Ethyl S-(−)-lactate (45 g, 0.381 mole) and benzyl 2,2,2-trichloroacetimidate (97 g, 0.385 mole) were mixed in 150 mL of dichloromethane and 300 mL of hexanes. The solution was stirred and chilled to 0° C. in an ice-water bath, followed by dropwise addition of trifluoromethanesulfonic acid (1.5 mL). White precipitate started to appear upon the addition of trifluoromethanesulfonic acid. The reaction mixture was allowed to warm up to room temperature gradually and stirred at room temperature overnight. The unsoluable white solid was filtered off. The resulting filtrate was washed with water, 10% NaHCO$_3$, brine and dried over anhydrous MgSO$_4$. Removal of solvent afforded 70 g of light brown liquid (88%). $^1$H-NMR analysis indicated that it was pure enough for next step without further purification. $^1$H-NMR (Varian 300 MHz spectrometer, CDCl$_3$, ppm): 7.3–7.4 (m, 5H), 4.69–4.71 (d, 1H), 4.44–4.47 (d, 1H,), 4.20–4.25 (m, 1H), 4.03–4.07 (q, 2H), 1.43–1.45 (d, 3H), 1.28–1.31 (t, 3H).

b) Reduction of the Ester Group: Under a nitrogen atomsphere, a solution of 33 g of the crude product from above step (0.159 mole) in 50 mL of anhydrous THF was added dropwise to a stirred suspension of LiAlH$_4$ (6 g, 0.158 mole) in 150 mL of anhydrous THF in a 3-neck round bottom flask equipped with a condenser (Caution: the reaction was exothermic!). The reaction mixture was stirred for an additional hour after the addition of LiAlH$_4$, followed by dropwise addition of 50 mL of ethyl acetate to quench any excess LiAlH$_4$. The reaction mixture was then poured into a mixture of 900 mL crushed ice and 100 mL of concentrated H$_2$SO$_4$. Separated aqueous layer was extracted with 3×200 mL of ether. Combined organic solution was washed with brine and dried over MgSO$_4$. Removal of solvent afforded 20 g of light brown liquid (76%). $^1$H-NMR analysis indicated that it was pure enough for next step without further purification. $^1$H-NMR (Varian 300 MHz spectrometer, CDCl$_3$, ppm): 7.13–7.40 (m, 5H), 4.66–4.68. (d, 1H), 4.49–4.51 (d, 1H), 3.68–3.70 (m, 1H), 3.60–3.65 (m, 1H), 3.51–3.54 (m, 1H), 1.19–1.20 (d, 3H).

c) Tosylation of the Primary Hydroxyl Group: Crude product from above step (20 g, 0.12 mole) was dissolved in 200 mL of pyridine at room temperature, followed by addition of tosyl chloride (25 g, 0.13 mole) in small portions. The reaction mixture was stirred at room temperature overnight. The reaction mixture was then poured into a mixture of 600 mL crushed ice and 300 mL of concentrated HCl. Separated aqueous layer was extracted with 3×200 mL of ether. Combined organic solution was washed with brine and dried over MgSO$_4$. Removal of solvent afforded 31.2 g of light brown liquid (81%). $^1$H-NMR analysis indicated that it was pure enough for next step without further purification. $^1$H-NMR (Varian 300 MHz spectrometer, CDCl$_3$, ppm): 7.95–7.98 (d, 2H), 7.42–7.58 (m, 7H), 4.68–4.69 (d, 2H), 4.18–4.20 (m, 2H,), 3.93–3.97 (m, 1H), 2.62 (s, 3H), 1.34–1.36 (d, 3H).

d) Alkylation of p-Toluenesulfonamide: A mixture of the tosylate from above step (16 g, 50 mmol), p-toluenesulfonamide (4.2 g, 25 mmol) and 56% aqueous KOH (12.5 mL) in 150 mL of DMSO was stirred at 100° C. for 5 hours. After cooled to room temperature, it was poured into 200 mL of 20% aqueous NH$_4$Cl solution and then extracted with 3×200 mL of ethyl acetate. Combined extracts were washed with brine and dried over anhydrous MgSO$_4$. Solvent was removed under reduced pressure. The residue was purified by silica gel column chromatography. 6.5 g of light yellow liquid was obtained (56%). $^1$H-NMR (Varian 300 MHz spectrometer, CDCl$_3$, ppm): 7.85–7.88 (d, 2H), 7.38–7.48 (m, 12H), 4.62–4.66 (d, 2H), 4.39–4.43 (d, 2H,), 3.92–3.96 (m, 2H), 3.51–3.54 (m, 4H), 2.56 (s, 3H), 1.28–1.30 (d, 6H).

e) Removing of the Benzyl Groups: Purified product from above step (11.5 g, 24.6 mmol) was dissolved in 150 mL of chloroform and cooled to 0° C. in an ice-water bath. Trimethylsilyl iodide (16 mL) was then added dropwise. The reaction mixture was allowed to warm up to room temperature and stirred for 3 hours. The dark brown reaction mixture was poured into 200 mL of ice-water and extracted with 3×250 mL of ether. Combined ether solution was washed brine, 20% sodium thiosulfate solution and dried over anhydrous MgSO₄. Removal solvent afforded a semi-solid residue. The solid was collected by filteration and washed with 20% ethyl acetate in hexanes. 4.5 g of off-white solid was obtained (64%). ¹H-NMR (Varian 300 MHz spectrometer, CDCl₃, ppm): 7.69–7.71 (d, 2H), 7.32–7.35 (d, 2H), 4.10–4.20 (m, 2H), 3.00–3.03 (m, 4H,), 2.44 (s, 3H), 1.18–1.20 (d, 6H).

f) Tosylation of Hydroxyl Group in Chiral Diol: To the solution of chiral diol (1 mmol) in pyridine (5 ml) was added tosyl chloride (5.5 mmol) at 0° C., the reaction mixture was stirred overnight. Add water, extracted with DCM (3×), the DCM layer was washed with 3N HCl, followed by brine. Dried over Na₂SO₄. The crude product was purified by column chromatography and give 70–76% yield of tritosylate. LC-MS: 596 (calc. 595.75)

g) Preparation of Phosphane Borane Intermediate: To a stirred solution of 1 mmol C₆H₄(PH₂)₂ in 10 ml DMSO, under nitrogen atmosphere, was added 56% KOH (2.1 mmol), followed by the solution of tritosylate (1.8 mmol) in 10 ml DMSO, stirred at 75° C. for 30 min, and another 4 mmol 56% KOH was added. Heating was continued at 75° C. for another 4 h. To the reaction mixture was added saturated NH4Cl, the mixture was extracted with EtOAc (3×). The combined organic phase was washed twice with brine, dried over MgSO₄ and evaporated to give crude product. The crude product was stirred with 1M borane THF solution overnight. The THF was removed on evaporator. The residue was partitioned between brine and ethyl acetate. The aqueous layer was extracted with ethyl acetate (2×), the combined organic phase was washed with brine and dried over MgSO₄. The crude product was purified by column and give 37.5% yield of desired phosphine borane intermediate. LC-MS: found 659 (calc. 658.60), δ³¹PNMR(CDCl₃): 19.249 (s), −18.544 (d, J=28.75 Hz). [α]²⁰₅₈₉=−98.6° (c 1.03, CHCl₃)

h) The phosphane borane intermediate was deboraned by stirring with DABCO (1 eq.) in benzene at 50° C. for 2 hours.

Example II and III

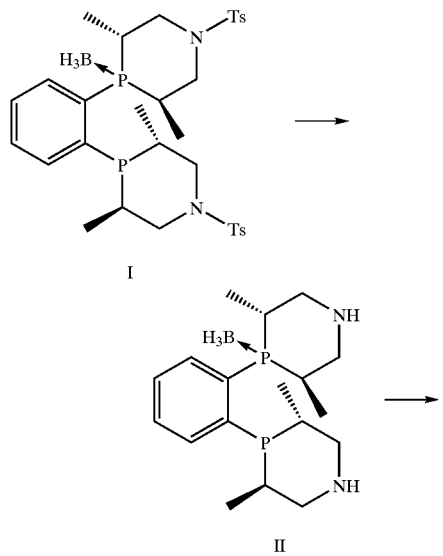

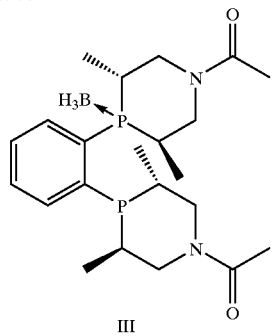

III

To 0.5 mmol of the phosphine borane intermediate I prepared in accordance with Example I was added 1M LiAlH₄/THF solution (10 ml) at rt. the mixture was stirred at room temperature and followed by LC-MS. After reaction is complete, quenched with water. Then 3 eq. of Acetic anhydride was added. The reaction mixture was stirred at r.t. for 4 hours. General work up and the crude product was purified by column chromatography. The product was deboraned by stirring with DABCO (1 eq.) in benzene at 50° C. for 2 hour. LC-MS: found 421 (calc. 420.47). δ¹HNMR(CDCl₃): 7.45 (m, 4H, Ph), 5.00 (m, 2H), 4.03 (m, 2H), 3.83 (m, 1H), 3.28 (m, 1H), 2.40–2.90 (m, 6H), 2.25 (6H, Ac) δ³¹PNMR (CDCl₃): −14.70 (d, J=3.04 Hz), −15.61 (d, J=13.73 Hz).

Example IV

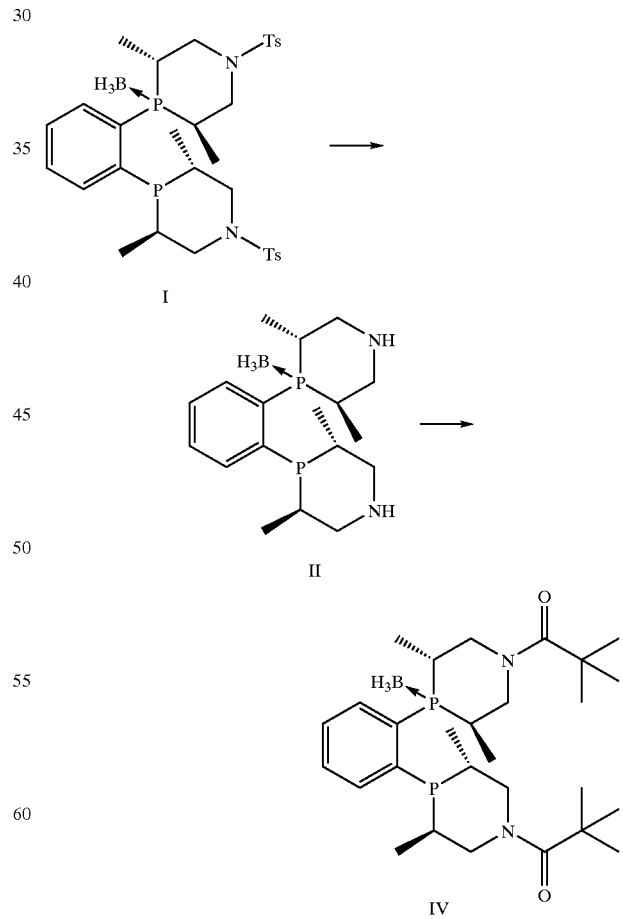

To 0.5 mmol of the phosphine borane intermediate I prepared in Example I was added 1M LiAlH₄/THF solution (10 ml) at rt. the mixture was stirred at room temperature and followed by LC-MS. After reaction is complete, quenched with water. Then 3 eq. of pivaloyl chloride was added, followed by 3 eq of $K_2CO_3$. The reaction mixture was stirred at r.t. for 4 hours. General work up and the crude product was purified is by column chromatography. The product was deborane by stirring with DABCO (1 eq.) in benzene at 50° C. for 2 hour. R=tBu: LC-MS: found 505 (calc: 504.62). $\delta^1$HNMR(CDCl$_3$): 7.48 (m, 4H, Ph), 4.94 (m, 2H), 4.59 (m, 2H), 3.25 (m, 4H), 2.87 (m, 2H), 2.59 (m, 2H), 0.93, 1.20, 1.50 (m, 30H, CH$_3$). $\delta^{31}$PNMR(CDCl$_3$): −15.249 (s).

Example V

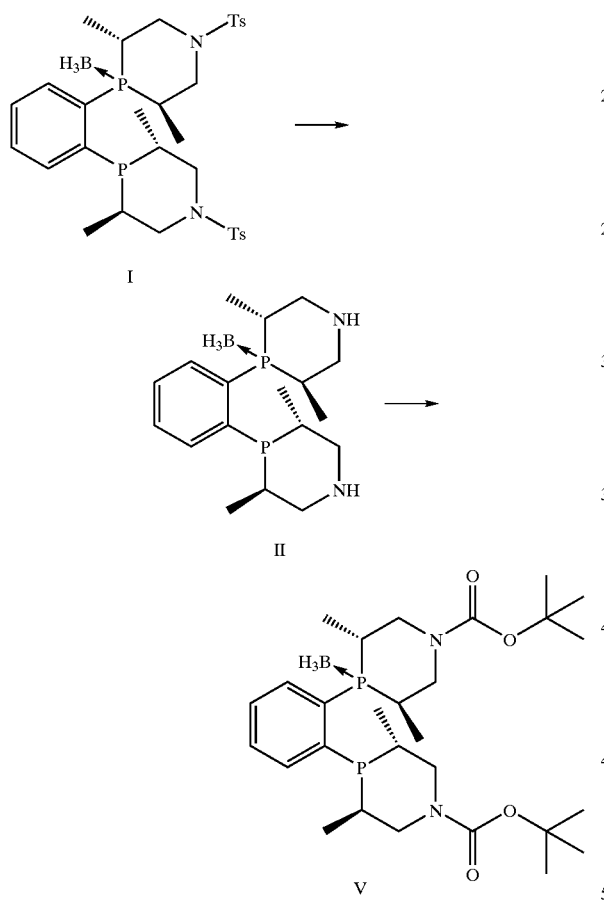

To the phosphine borane intermediate of example I (0.5 mmol) was added 1M LiAlH$_4$/THF solution (10 ml) at rt. the mixture was stirred at room temperature and followed by LC-MS. After reaction is complete, quenched with water. Then 3 eq. of Boc$_2$O was added, followed by 3 eq of K$_2$CO$_3$. The reaction mixture was stirred at r.t. for 4 hours. General work up and the crude product was purified by column chromatography. The product was deboraned by stirring with DABCO (1 eq.) in benzene at 50° C. for 2 hours. R=$^t$BuO: LC-MS: found 537 (calc. 536.62). $\delta^1$HNMR (CDCl$_3$): 7.30 (m, 4H, Ph), 4.06–4.50 (m, 5H), 3.38 (m, 2H), 2.40–2.70 (m, 5H), 1.44 (s, 18H), 0.99 (d, 6H, J=9.00 Hz, CH$_3$), 0.77 (m, 6H, CH$_3$). $\delta^{31}$PNMR(CDCl$_3$): −15.537 (s).

Example VI

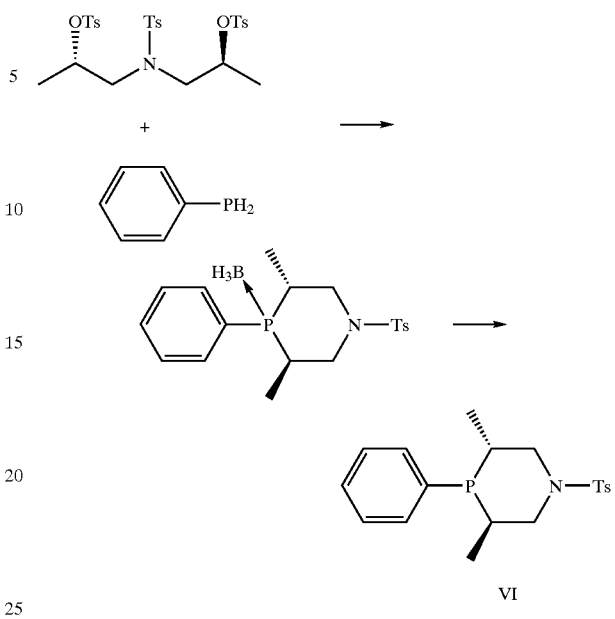

To a stirred solution of 1 mmol C$_6$H$_4$PH$_2$ in 5 ml DMSO, under nitrogen atmosphere, was added 56% KOH (1.1 mmol), followed by the solution of tritosylate (0.95 mmol) in 10 ml DMSO, stirred at 75° C. for 30 min, and another 2 mmol 56% KOH was added. Heating was continued at 75° C. for another 4 h. To the reaction mixture was added saturated NH4Cl, the mixture was extracted with EtOAc (3×). The combined organic phase was washed twice with brine, dried over MgSO$_4$ and evaporated to give crude product. The crude product was stirred with 1M borane THF solution overnight. The THF was removed on evaporator. The residue was partitioned between brine and ethyl acetate. The aqueous layer was extracted with ethyl acetate (2×), the combined organic phase was washed with brine and dried over MgSO$_4$. The crude product was purified by column and gave the desired phosphine borane intermediate VI. The product was deboraned by stirring with DABCO (1 eq.) in benzene at 50° C. for 2 hours Having described the invention we claim:

1. A chiral phosphine compound of the formula

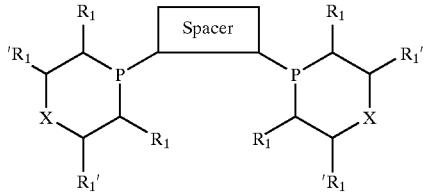

Formula 2 wherein Spacer is a molecule having two functional groups each capable of attaching to a phosphorus atom on a six-membered phosphaline ring;

wherein X is selected from the group consisting of oxygen, sulfur, methylene (—CH$_2$—), —NR$_3$, and PR$_3$;

wherein R$_1$ is selected from a group consisting of substituted alkyl, substituted alkenyl substituted alkynyl, substituted aryl, and substituted alkylaryl;

R$_1$' is selected from a group consisting of hydrogen, substituted alkyl, substituted alkenyl substituted alynyl, substituted aryl, and substituted alkylaryl; and wherein R₃ is selected from a group consisting of hydrogen, substituted alkyl, substituted alkenyl, substituted alkynyl, substituted aryl, substituted alkylaryl.

2. The compound of claim 1, wherein said spacer is —(CH$_2$)$_n$— wherein n is an integer ranging from 2 to 6.

3. The compound of claim 1, wherein said spacer is —(CH$_2$)$_m$X(CH$_2$)$_n$— wherein m and n are integers ranging from 1 to 6 and X is selected from a group consisting of oxygen, sulfur, (—CH$_2$—), —NR$_3$, and PR$_3$.

4. The compound of claim 1, wherein said spacer is selected from a group consisting of 1,2-divalent phenyl; 1,2-divalent phenyl substituted with alkyl (with 1–8 carbon atoms), aryl, and alkyl aryl.

5. The compound of claim 1, wherein said spacer is selected from a group consisting of 1,2-divalent napthyl; 1,2-divalent napthyl substituted with alkyl (with 1–8 carbon atoms), aryl, and alkyl aryl.

6. The compound of claim 1, wherein said spacer is selected from a group consisting of 2,3-divalent napthyl; 2,3-divalent napthyl substituted with alkyl having 1–8 carbon atoms, aryl, and alkyl aryl.

7. The compound of claim 1, wherein said spacer is selected from a group consisting of 1–8-divalent napthyl; 1,8-divalent napthyl substituted with alkyl having 1 to 8 carbon atoms, aryl, and alkyl aryl.

8. The compound of claim 1, wherein said spacer is selected from a group consisting of 2,2'-divalent 1,1'-biphenyl; 2,2'-divalent 1,1'-biphenyl substituted with alkyl having 1 to 8 carbon atoms, aryl, and alkyl aryl.

9. A chiral phosphine compound of the formula

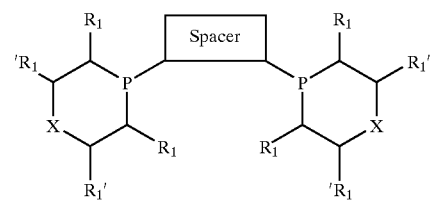

Formula 2 wherein Spacer is a molecule having two functional groups each capable of attaching to a phosphorus atom(s) on a six-membered phosphaline ring;

wherein X is selected from the group consisting of oxygen, sulfur, methylene (—CH$_2$—), NR$_3$, and PR$_3$;

wherein R$_1$ is selected from a group consisting of substituted alkyl, substituted alkenyl, substituted alkynyl, substituted aryl, and substituted alkylaryl;

wherein R$_1$' is selected from the group consisting of hydrogen, substituted alkyl, substituted alkenyl, substituted alkynyl, substituted aryl, and substituted alkylaryl; and wherein R$_3$ is selected from a group consisting of substituted alkyl sulfonyl, substituted aryl sulfonyl, substituted alkyl carboxyl, substituted aryl carboxyl, substituted alkoxyl carboxyl, substituted aroxyl carboxyl substituted alkyl carboxamido, substituted aryl carboxamido, substituted alkylthio carboxamido, and substituted arylthio carboxamido.

* * * * *